(12) United States Patent
Zumbrum et al.

(10) Patent No.: US 11,660,438 B2
(45) Date of Patent: May 30, 2023

(54) SEPARABLE FLUID TRANSFER CONNECTOR

(71) Applicant: Sartorius Stedim North America Inc., Bohemia, NY (US)

(72) Inventors: Michael A. Zumbrum, New Oxford, PA (US); Johannes Wortmeyer, Goettingen (DE)

( * ) Notice: Subject to any disclaimer, the term of this patent is extended or adjusted under 35 U.S.C. 154(b) by 706 days.

(21) Appl. No.: 16/562,533

(22) Filed: Sep. 6, 2019

(65) Prior Publication Data

US 2021/0071791 A1 Mar. 11, 2021

(51) Int. Cl.
*A61M 39/10* (2006.01)
*F16L 21/00* (2006.01)
*F16L 47/02* (2006.01)
*F16L 31/02* (2006.01)

(52) U.S. Cl.
CPC .............. *A61M 39/10* (2013.01); *F16L 21/00* (2013.01); *F16L 31/02* (2013.01); *F16L 47/02* (2013.01)

(58) Field of Classification Search
CPC .......... B29C 57/10; F16L 55/10; F16L 47/02; F16L 47/20; F16L 47/22; F16L 13/141; F16L 33/2076; F16L 31/00; A61M 39/146
USPC .......................................................... 138/99
See application file for complete search history.

(56) References Cited

U.S. PATENT DOCUMENTS

| | | | |
|---|---|---|---|
| 2,776,473 A | 1/1957 | Dailey et al. | |
| 3,276,447 A | 10/1966 | Hamilton | |
| 3,516,690 A * | 6/1970 | Kreig | F16L 13/0236 |
| 4,109,944 A * | 8/1978 | Curtin | F16L 47/02 |
| 5,345,070 A * | 9/1994 | Hlavinka | B29C 65/743 |
| 5,520,218 A | 5/1996 | Hlavinka et al. | |
| 6,779,575 B1 † | 8/2004 | Arthun | |
| 8,056,583 B2 † | 11/2011 | Lofving | |
| 2008/0149503 A1 | 6/2008 | Pandori | |

(Continued)

FOREIGN PATENT DOCUMENTS

EP 2677223 B1 † 8/2015

OTHER PUBLICATIONS

International Search Report and the Written Opinion of the International Searching Authority for PCT/US19/49846; dated Jan. 21, 2020.

(Continued)

*Primary Examiner* — Zachary T Dragicevich
(74) *Attorney, Agent, or Firm* — Womble Bond Dickinson (US) LLP

(57) ABSTRACT

A connector for facilitating fluid transfer includes first fitting, a second fitting, a rigid conduit, a first retaining connector, and a second retaining connector. The rigid conduit includes a flexible tube surrounded by a deformable sleeve. The rigid conduit is connected on a first end to the first fitting and on a second end to the second fitting. The first retaining connector connects the first fitting to the rigid conduit and the second retaining connector connects the second fitting to the rigid conduit. A lumen extends through the rigid conduit and is capable of being sealed. The rigid conduit and the flexible tube are capable of being severed while maintaining the seal of the lumen to separate the first fitting from the second fitting. The connections of the first fitting and the second fitting to the rigid conduit are capable of withstanding at least 1 bar of pressure without leaking.

28 Claims, 5 Drawing Sheets

(56) References Cited

U.S. PATENT DOCUMENTS

| | | |
|---|---|---|
| 2011/0155274 A1 | 6/2011 | Zumbrum |
| 2014/0103077 A1 | 4/2014 | Zumbrum |
| 2017/0009920 A1 | 1/2017 | Canatella |
| 2017/0191597 A1* | 7/2017 | Conrad ................. F16L 51/025 |

OTHER PUBLICATIONS

European Search Report for EP Application No. 19944340.9-1122 / 4025292 PT/US2019049846, dated Mar. 21, 2023, 3 pages.

\* cited by examiner
† cited by third party

SEPARABLE FLUID TRANSFER CONNECTOR

STATEMENT OF RELATED CASES

The present disclosure relates to the following patent disclosures presently co-owned with the current disclosure: U.S. Pat. Nos. 8,505,586 and 10,006,567; International Patent Publications WO2015084388 and WO2019147223; and U.S. Patent Publication Nos. 2018/0238475 and 2018/0297753 each of which is incorporated by reference herein in their entirety.

TECHNICAL FIELD

This disclosure relates generally to aseptic fluid transfer assemblies, and more particularly to separable connections of aseptic fluid transfer assemblies.

BACKGROUND

Biopharmaceutical and pharmaceutical drug developers and manufactures often develop and manufacture products in a fluid form. These products must be handled with care to maintain an aseptic environment and avoid contamination. Biopharmaceutical and pharmaceutical companies use manufacturing processes that often require transfer fluid into or out of a closed processing system while maintaining a substantially aseptic, hygienic, or sterile environment. For example, fluid components may be added to large processing tanks during various stages of the manufacturing process. Similarly, samples are often drawn from each batch throughout the manufacturing process to keep a close watch on characteristics including but not limited to cell viability, density and characterization, fluid chemistry, pH, and sterility. To avoid contamination, it is preferred that the entire fluid pathway from the processing tank to the sample collection vessel or source container should remain aseptic.

In some instances, disconnecting the sample collection vessel from the tank may be required. The disconnection should avoid exposing the sample to the environment, including ambient air, and resulting in sealing of the sample collection vessel and the remainder of fluid retention and transfer system, e.g., the tank, respectively.

The present disclosure describes further improvements to maintain aseptic environments and avoid contamination after separating portions of a closed aseptic system.

SUMMARY

In accordance with an embodiment of the present disclosure, a connector for facilitating fluid transfer includes a first fitting, a second fitting, a rigid conduit, a first retaining connector, and a second retaining connector. The rigid conduit includes a flexible tube surrounded by a deformable sleeve. The rigid conduit is connected on a first end to the first fitting and on a second end to the second fitting. The first retaining connector connects the first fitting to the rigid conduit and the second retaining connector connects the second fitting to the rigid conduit. A lumen extends through the rigid conduit and is capable of being sealed. The rigid conduit and the flexible tube are capable of being severed while maintaining the seal of the lumen to separate the first fitting from the second fitting. The connections of the first fitting and the second fitting to the rigid conduit are capable of withstanding at least 1 bar of pressure without leaking.

In embodiments, the deformable sleeve is formed of a material that has a plasticity such that pressure applied to the deformable sleeve causes the deformable sleeve to deform about and seal the flexible tube and upon continued application of pressure to the deformable sleeve, the deformable sleeve and the flexible tube are cut and the deformable sleeve retains a deformed shape substantially sealing the tube. The deformable sleeve may be adhesively attached to the flexible tube. The deformable sleeve and the adhesive may be formed of materials that have a plasticity such that the pressure applied to the deformable sleeve causes the deformable sleeve and the adhesive to deform about and seal the flexible tube and upon continued application of pressure to the deformable sleeve, the deformable sleeve, the adhesive, and the flexible tube are cut and the deformable sleeve retains a deformed shape to substantially seal the flexible tube.

In some embodiments, the flexible tube is integral with at least one of the first fitting or the second fitting. The flexible tube may be integral with both the first and second fittings. The rigid conduit is clamped to at least one of the first fitting or the second fitting. The rigid conduit may be connected to at least one of the first fitting or the second fitting with a fastener comprising a crimp collar that surrounds an elastomeric liner. The deformable sleeve may be attached to the flexible tube with an adhesive selected from the group consisting of a curable platinum catalyzed silicone adhesive, a moisture curable silicone adhesive, a hot melt adhesive, cyanoacrylate, epoxy, and urethane. The rigid tube may comprise a primer between the flexible tube and the adhesive.

In certain embodiments, the deformable sleeve is made of a metal selected from the group consisting of aluminum, anodized aluminum, brass, bronze, nickel-plated bronze, and stainless steel. The deformable sleeve may have a wall thickness in a range of 0.005 to 0.062 inches.

In particular embodiments, the flexible tube is constructed from material selected from the group consisting of styrene isobutylene copolymer and ethylene propylene copolymers blended with polypropylene. The flexible tube may comprise thermoplastic polymer tubing. The flexible tube may be constructed from material selected from the group consisting of polyvinyl chloride (PVC) and a flexible polyolefin. The flexible tube may comprise a primer between the flexible tube and the adhesive. The flexible tube may include thermoset elastomer tubing. The flexible tube may be constructed from material selected from the group consisting of silicone, phenyl silicone, fluoroelastomer (FKM), perfluoroelastomer (FFKM), and perfluoropolyether.

In some embodiments, the first fitting and the second fitting are selected from the group consisting of barb fittings, elbow fittings, tri-clamp fittings, quick connect fittings, aseptic fittings, threads, and quick couplers. The rigid conduit is non-linear between the first and second ends thereof. The rigid conduit may include a bend between the first and second ends thereof. The bend may be in a range of 15 degrees to 90 degrees.

In another embodiment of the present disclosure, an aseptic fluid transfer system includes a first vessel, a second vessel, and a conduit. The conduit includes a first fitting, a second fitting, and a rigid conduit. The first fitting is in fluid communication with the first vessel and the second fitting is in fluid communication with the second vessel. The rigid conduit is connected between the first and second fittings. A lumen extends through the rigid conduit and is capable of being sealed. The rigid conduit is capable of being severed while maintaining a seal of the lumen to separate the first fitting from the second fitting.

In another embodiment of the present disclosure, a method of aseptically separating a closed fluid transfer system, the closed fluid transfer system includes a first vessel, a second vessel, and a fluid transfer connector that is disposed between the first vessel and the second vessel. The first transfer connector has a first fitting that is suitable for receiving a fluid from the first vessel, a second fitting that is suitable for emitting the fluid to the second vessel, and a rigid conduit that is connected between the first and second fittings. The method includes applying pressure to the rigid conduit to deform the rigid conduit and applying further pressure to the rigid conduit to cut the rigid conduit thereby leaving the rigid conduit substantially sealed where cut.

In embodiments, the rigid conduit includes a flexible tube that is surrounded by a deformable sleeve. The deformable sleeve may be adhered to the flexible tube. Deforming the rigid conduit may comprise deforming the flexible tube and the deformable sleeve. Sealing the rigid conduit may comprise sealing the flexible tube. The pressure to deform and the pressure to cut may be applied simultaneously.

In another embodiment of the present disclosure, a connector for facilitating fluid transfer includes a rigid conduit, a first fitting, a second fitting, a first retaining connector, and a second retaining connector. The rigid connector includes a flexible tube surrounded by a deformable sleeve. The rigid conduit has a first end, a second end, and a lumen defined therethrough. The rigid conduit is configured to seal the lumen when severed. The first retaining connector forms a first connection between the first fitting and the first end of the rigid conduit. The first connection is capable of withstanding at least 1 bar of pressure without leaking. The second retaining connector forms a second connection between the second fitting and the second end of the rigid conduit. The second connection being capable of withstanding at least 1 bar of pressure without leaking. The rigid conduit may be non-linear between the first and second ends thereof. The rigid conduit includes a bend between the first and second ends thereof. The bend may be in a range of 15 degrees to 90 degrees.

In another embodiment of the present disclosure, a connector for facilitating fluid transfer includes a rigid conduit, a first fitting, and a second fitting. The rigid conduit includes a flexible tube surrounded by a deformable sleeve. The rigid conduit has a first end, a second end, and a lumen defined therethrough. The rigid conduit is configured to seal the lumen when severed. The rigid conduit includes a bend between the first and second ends thereof. The first fitting is connected to the first end of the rigid conduit. The second fitting is connected to the second end of the rigid conduit.

In embodiments, the bend is in a range of 15 degrees to 90 degrees. The connector may include a first retaining connector that forms a first connection between the first fitting and the first end of the rigid conduit. The first connection may be capable of withstanding at least 1 bar of pressure without leaking. The connector may include a second retaining connector may form a second connection between the second fitting and the second end of the rigid conduit. The second connection is capable of withstanding at least 1 bar of pressure without leaking.

In some embodiments, the deformable sleeve is formed of a material that has plasticity such that the deformable sleeve is configured to deform about and seal the lumen in response to a pressure applied to the deformable sleeve and is configured to retain a deformed shape to seal the lumen when the rigid conduit is cut in response to additional pressure being applied to the deformable sleeve.

In particular embodiments, the deformable sleeve is adhesively attached to the flexible tube. The adhesive is selected from the group consisting of a curable platinum catalyzed silicone adhesive, a moisture curable silicone adhesive, a hot melt adhesive, cyanoacrylate, epoxy, and urethane. The flexible tube may comprise a primer between the flexible tube and the adhesive.

In certain embodiments, the flexible tube of the rigid conduit is integral with the first fitting or the second fitting. The flexible tube of the rigid conduit may be integral with both the first fitting and the second fitting. The rigid conduit may be clamped to at least one of the first fitting or the second fitting. The rigid conduit may be connected to at least one of the first fitting or the second fitting with a fastener comprising a crimp collar that surrounds an elastomeric liner.

In particular embodiments, the deformable sleeve is made of a metal selected from the group consisting of aluminum, anodized aluminum, brass, bronze, nickel-plated bronze, and stainless steel. The deformable sleeve may have a wall thickness of between 0.005 to 0.062 inches. The flexible tube may comprise a thermoplastic elastomer tubing. The flexible tube may be constructed from material selected from the group consisting of styrene isobutylene copolymer and ethylene propylene copolymers blended with polypropylene. The flexible tube may comprise thermoplastic polymer tubing. The flexible tube may be constructed from material selected from the group consisting of polyvinyl chloride (PVC) and a flexible polyolefin. The flexible tube may comprise thermoset elastomer tubing. The flexible tube may be constructed from material selected from the group consisting of silicone, phenyl silicone, fluoroelastomer (FKM), perfluoroelastomer (FFKM), and perfluoropolyether.

In certain embodiments, the first and second fittings are selected from the group consisting of barb fittings, elbow fittings, tri-clamp fittings, quick connect fitting, aseptic fittings, threads, and quick couplers.

These and other aspects of the present invention will become apparent to those skilled in the art after a reading of the following description of the preferred embodiments, when considered in conjunction with the drawings. It should be understood that both the foregoing general description and the following detailed description are explanatory only and are not restrictive of the invention as claimed.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
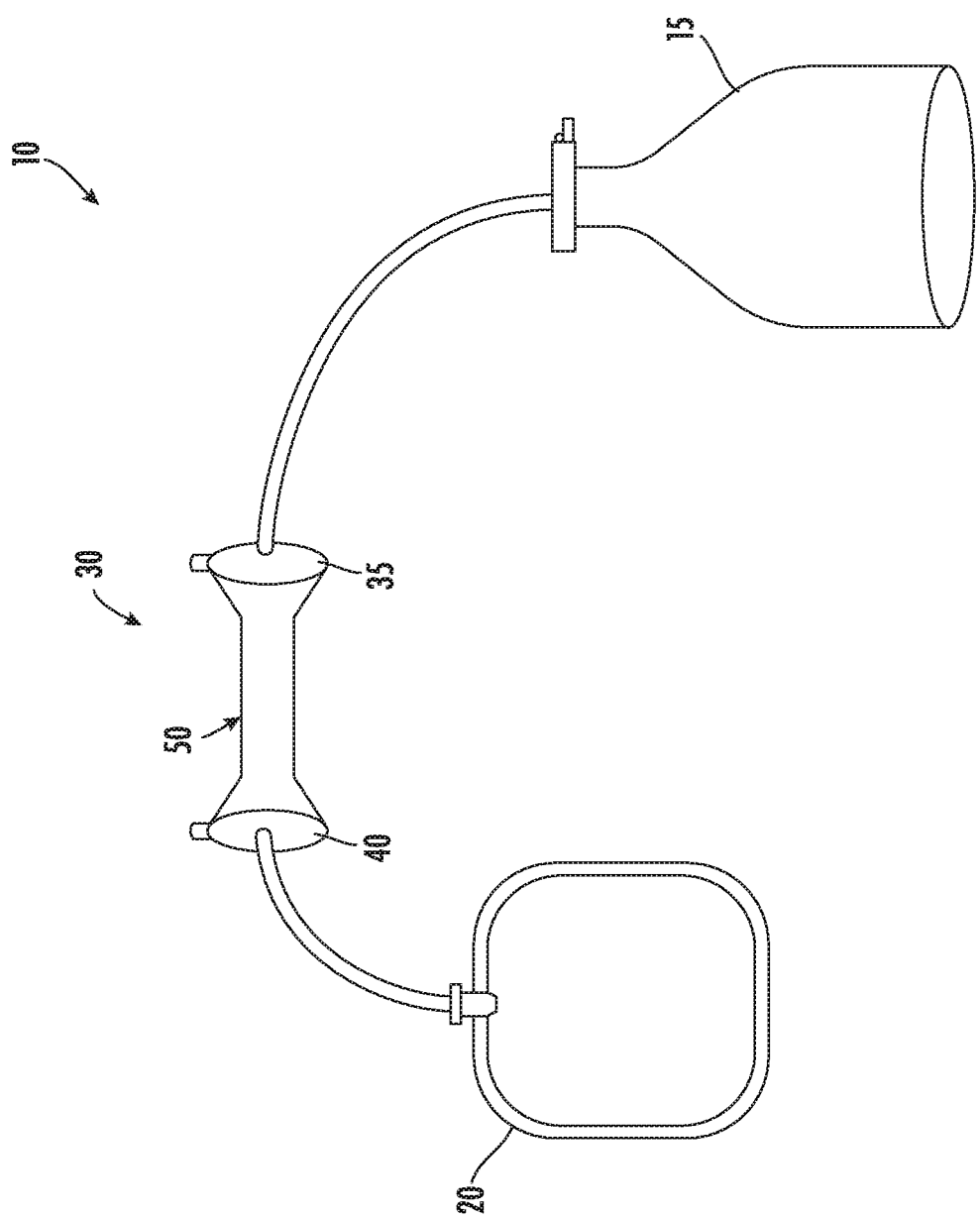
FIG. 1 shows an example closed aseptic system with a connector according to an embodiment of the present disclosure.

The present disclosure is now described more fully hereinafter with reference to example embodiments thereof with reference to the drawings in which like reference numerals designate identical or corresponding elements in each of the several views. These example embodiments are described so that this disclosure will be thorough and complete, and will fully convey the scope of the disclosure to those skilled in the art. Features from one embodiment or aspect can be combined with features from any other embodiment or aspect in any appropriate combination. For example, any individual or collective features of method aspects or embodiments can be applied to apparatus, product, or component aspects or embodiments and vice versa. The disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the," and the like include plural referents unless the context clearly dictates otherwise. In addition, while reference may be made herein to quantitative measures, values, geometric relationships or the like, unless otherwise stated, any one or more if not all of these may be absolute or approximate to account for acceptable variations that may occur, such as those due to manufacturing or engineering tolerances or the like.

FIG. 1 shows an exemplary aseptic fluid transfer system 10 including a first vessel 15 and a second vessel 20. In use, the fluid transfer system 10 is configured to allow at least one transfer of a fluid between the first vessel 15 and the second vessel 20 through at least one connector 30. In one embodiment, the fluid transfer system 10 is a closed, aseptic system. As used herein, "aseptic" means free from contamination, e.g., contamination caused by bacteria, viruses, or other microorganisms. Various processes may be used for rendering the fluid transfer system aseptic, e.g., gamma radiation. In another embodiment, the fluid transfer system 10 or components thereof may be rendered aseptic by exposure to steam above 121° C. for a period of time long enough to eliminate microorganisms. In yet another embodiment, the fluid transfer system 10 or components thereof may be rendered aseptic by chemical treatment, such as with ethylene oxide (ETO). With respect to the use of gamma radiation, the fluid transfer system may be packaged in a first package, irradiated and rendered aseptic, and then placed in a second package. With respect to other methods, once rendered aseptic, the fluid transfer system may be appropriately packaged in a first package and stored in a second package to maintain the aseptic state until ready for use.

Suitable vessels for the first and second vessel 15, 20 can include, but are not limited to: sampling devices, containers, beakers, bottles, canisters, flasks, bags, receptacles, tanks, vats, vials, tubes, and the like that are generally used to contain fluids, slurries, and other similar substances.

Turning to FIGS. 2-6, the connector 30 is configured to provide a location along a fluid path from the first vessel 15 to the second vessel 20 where the fluid path may be sealed off and the first vessel 15 separated from the second vessel 20. The process of sealing off the fluid path may be a one-time process where the fluid path is not configured to be reopened or reconnected. The connector 30 may include a first fitting 35 configured to be in fluid communication with the first vessel 15 and a second fitting 40 configured to be in fluid communication with the second vessel 20. The first and second fittings 35, 40 may be barb fittings, elbow fittings, tri-clamp fittings, quick connect fittings, aseptic fittings (e.g., Opta® sterile connectors available from Sartorius AG), threads, quick couplers, or any other appropriate fittings known in the art. The first and second fittings 35, 40 may be made from a variety of materials, including thermoplastics such as polyolefins, polypropylene, polyethylene, polyoxymethylene (POM), polyvinylidenefluoride (PVDF), polytetrafluoroethylene (PTFE), polyamide, polysulfone, polyester, polycarbonate, or glass filled thermoplastics. The fittings may also be made from thermosets such as epoxies, pheonolics, silicone, or copolymers of silicone and novolacs. Other suitable materials may include cyanate ester, polyurethanes, or urethane methacrylate. Yet other metallic materials may be used for the fittings including stainless steel, aluminum, copper, or titanium. The fittings 35, 40 may be formed from molding, casting, additive manufacturing, or other known processes.

The connector 30 also includes a rigid conduit 50 connected between the first fitting 35 and the second fitting 40. As used herein, the term "rigid" means that certain pressures, discussed in greater detail herein, may be retained without damage to the conduit. Nevertheless, it is possible to cut with a tool or alike the conduit. In certain embodiments, the rigid conduit 50 is linear. However, as described below, the rigid conduit 50 may be non-linear.

Figure 3:
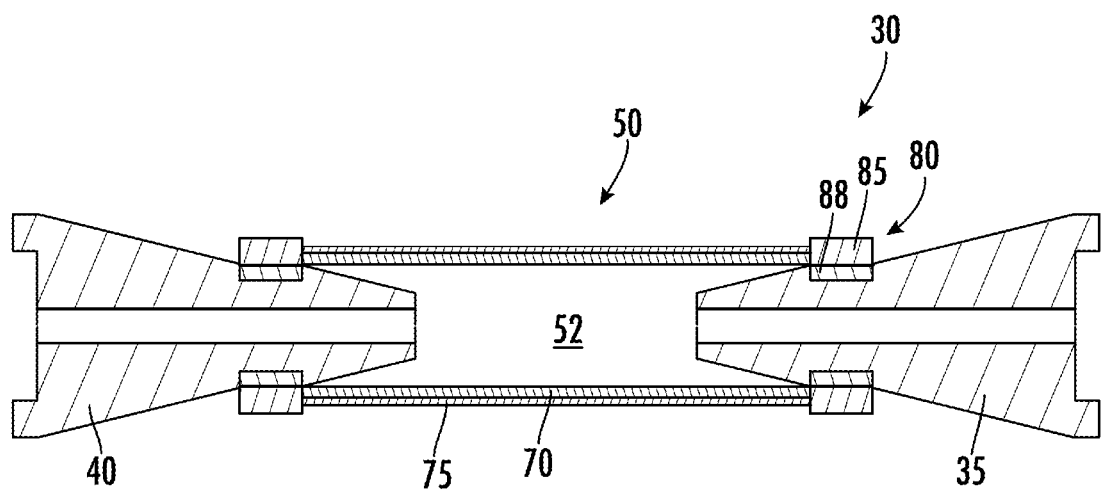
FIG. 3 is a schematic cross section of the connector of FIG. 2.

As shown in the cross section of FIG. 3, the rigid conduit 50 includes a lumen 52 defining a portion of the fluid pathway between the first and second fittings 35, 40, and therefore between the first and second vessels 15, 20. The lumen 52 is configured to be capable of being sealed off to close the fluid pathway. The act of sealing off the fluid pathway through the lumen 52 may result in severing the rigid conduit 50 to separate the first and second fittings 35, 40 while maintaining the seal of the lumen 52 to cap respective portions of the initial fluid pathway.

Staying with FIG. 3, the rigid conduit 50 comprises a flexible tube 70 and a deformable sleeve 75. The deformable sleeve 75 surrounds the length of the flexible tube 70. In one embodiment, the deformable sleeve 75 is fixed to the flexible tube 70. In another embodiment, the deformable sleeve 75 is fixed to the flexible tube 70 with an adhesive. The adhesive can help prevent the deformable sleeve 75 from slipping along the tube 70. The adhesive also couples the interior surface of the deformable sleeve 75 to the exterior surface of the tube 70. If the deformable sleeve 75 were not attached to the flexible tube 70, the deformable sleeve 75 could slip or pull away from the tube 70, especially as the deformable sleeve 75 is being deformed and ultimately cut, which could break the seal and allow the lumen 52 of the flexible tube 70 to open to the surrounding environment.

The deformable sleeve 75 comprises a wall having an interior surface. In one embodiment, the deformable sleeve 75 is made of a metal. The metal used to make the deformable sleeve 75 may be selected from the group consisting of aluminum, anodized aluminum, brass, bronze, nickel-plated bronze, and stainless steel. However, any suitable material may be used, including metals not listed above. Regardless of the material from which the deformable sleeve 75 is constructed, the material has a plasticity such that pressure applied to the flexible tube 70 at the location of the deformable sleeve 75 causes the deformable sleeve 75 to deform about and substantially seal the flexible tube 70 before the flexible tube 70 and deformable sleeve 75 are cut by continued application of pressure. The material of the deformable sleeve 75 also has plasticity such that once cut, the deformable sleeve 75 retains its deformed shape and thus substantially seals lumen 52 of the flexible tube 70. By sealing the lumen 52 at the point of cutting, any fluid in the lumen 52 is not exposed to the surrounding environment, thereby maintaining an aseptic environment for the fluid in vessel 15 and the fluid in vessel 20.

The wall thickness of the deformable sleeve 75 is understood to be dependent upon the material that forms the deformable sleeve 75. In one embodiment, the wall of the deformable sleeve 75 has a thickness of between about 0.008 and about 0.062 inches. In one embodiment, the deformable sleeve 75 is made from aluminum and has a wall thickness of from about 0.008 to about 0.062 inches. In another embodiment, the deformable sleeve 75 is made from anodized aluminum and has a wall thickness of from about 0.008 to about 0.062 inches. In yet another embodiment, the deformable sleeve 75 is made from bronze and has a wall thickness of from about 0.010 to about 0.032 inches. Depending on the material selected, the wall thickness will vary in order to maintain plasticity in the deformable sleeve 75 such that it may be substantially sealed and cut by application of a reasonable amount of pressure. A reasonable amount of pressure would be, for example, the amount of pressure that is applied by hand-tool, hydraulic tool, or other means that are appropriate for the wall thickness of the deformable sleeve 75. In an embodiment, the deformable sleeve 75 has a length of between about 1 and about 2 inches. However, the deformable sleeve 75 may be of any suitable length, and preferably extends substantially completely from the first fitting 35 to the second fitting 40.

In one embodiment, the flexible tube 70 is thermoplastic elastomer tubing such as a styrene isobutylene copolymer (C-Flex®) or ethylene propylene copolymers blended with polypropylene (Santoprene®). In another embodiment, the flexible tube 70 is made from a thermoplastic polymer such as polyvinyl chloride (PVC) or a flexible polyolefin such as Engage®. In another embodiment, the flexible tube 70 is made from a thermoset elastomer such as silicone, fluoro silicone, phenyl silicone, fluoroelastomer (FKM), perfluoroelastomer (FFKM), or perfluoropolyether (Sifel™). In yet another embodiment, the flexible tube 70 is made from a composite material such as a PTFE lined elastomer tube (SmartShield™ tubing), perfluoroalkoxy lined thermoplastic tubing (Bev-a-line®). Other material suitable to perform as flexible tube 70 may be selected and the listing above is not limiting.

The adhesive optionally fixing the deformable sleeve 75 to the tube 70 may be a silicone adhesive. In one embodiment, the silicone adhesive is curable platinum catalyzed silicone adhesive. In another embodiment, the silicone adhesive is moisture curable silicone adhesive. In one embodiment, the flexible tube 70 is primed before application of the adhesive and attaching to the deformable sleeve 75, thereby leaving a layer of primer between the flexible tube 70 and the deformable sleeve 75. Suitable primers are SS-4155 available from Momentive™, Med-162 available from NuSil Technology, and Rodorsil® V-O6C available from Bluestar Silicones. The primer may also operate to substantially seal the lumen 52 through the tube 70 upon the application of pressure and, ultimately, cutting of the flexible tube 70 and the deformable sleeve 75.

In another embodiment, the deformable sleeve 75 is attached to the flexible tube 70 with a hot melt adhesive. This is particularly useful for thermoplastic elastomer tubing. In another embodiment, the deformable sleeve 75 is attached to the flexible tube 70 using an adhesive selected from the group consisting of cyanoacrylate, epoxy, and urethane. These adhesives are particularly useful for thermoset elastomer tubing.

Figure 2:
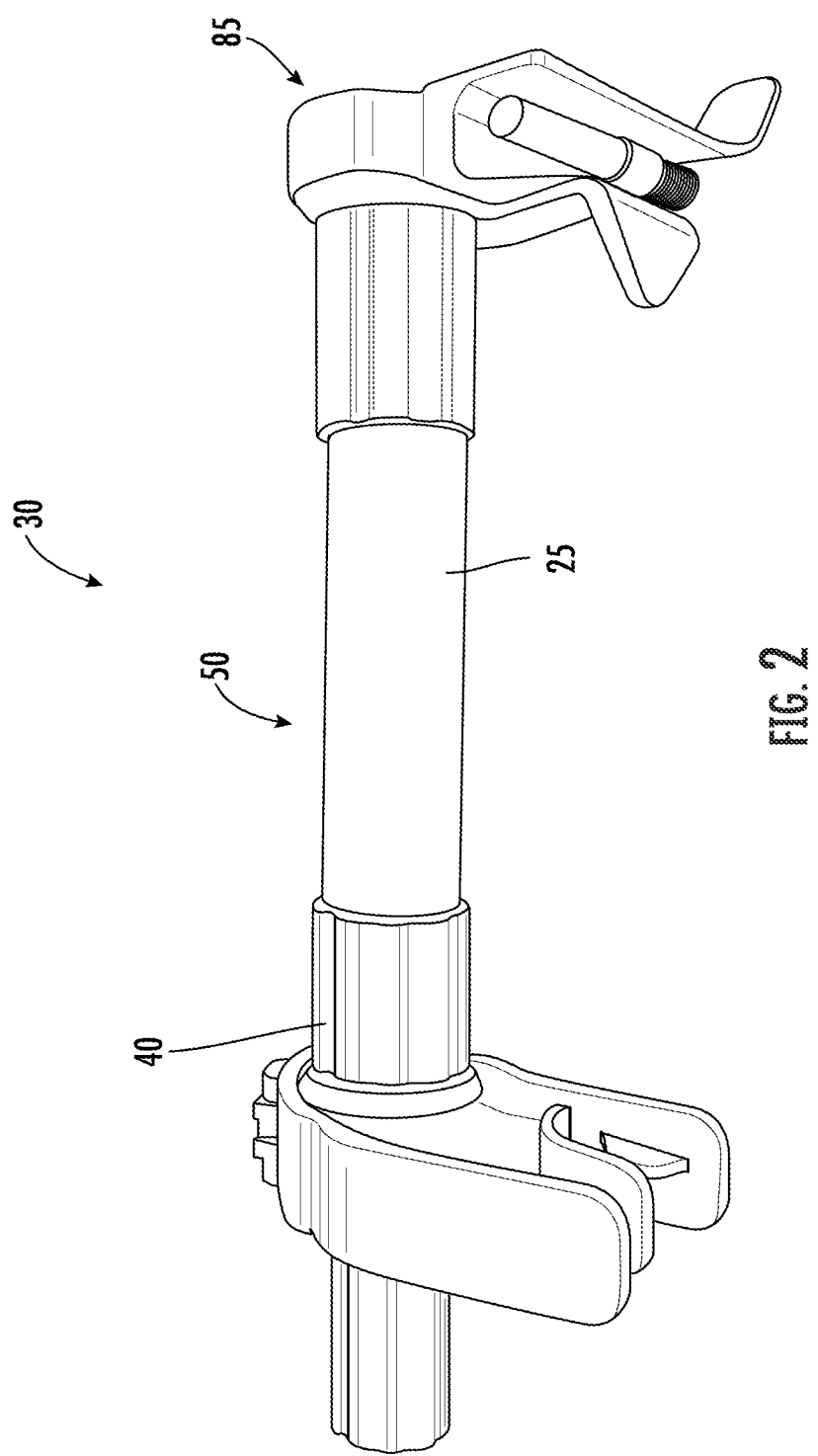
FIG. 2 is a detailed exterior view of the connector of FIG. 1.

In the embodiment of FIG. 2, the rigid conduit 50 is attached to each of the first and second fittings 15, 20 with a clamp 83, such as an Oetiker clamp, a cable tie, or a hose clamp and endless metal ring/clamp.

In the embodiment of FIG. 3, the rigid conduit 50 is attached to each of the first and second fittings 35, 40 with a fastener 80 that includes a crimp collar 85 that surrounds an elastomeric liner 88. The collar 85 is preferably formed from steel or stainless steel with a wall thickness of about 0.010 inches to about 0.100 inches. In one embodiment, the collar is formed using 3161 stainless steel and has a wall thickness of 0.049 inches and an outside diameter of 0.75 inches. The collar 85 provides a substantially rigid sleeve that may be permanently deformed using known crimping processes involving a hydraulic crimper. The collar 85 is configured to surround the elastomeric liner 88. The elastomeric liner 88 may be attached to or separate from the collar 85. In one embodiment, the elastomeric liner 88 is attached to an interior surface of the collar 85 with an adhesive layer. Unlike the deformable sleeve 75 of the rigid conduit 50, that is configured to be deformable by hand tools, the collar 85 is configured to be permanently crimped with a hydraulic crimper or other industrial machine.

The elastomeric liner 88 may be made from silicone (VMQ), or other materials such as phenyl silicone (PMVQ). The elastomeric liner 88 may maintain its elasticity at temperatures as low as −100° C. In one embodiment, the elastomeric liner 88 was formed from PMVQ using RTV MED-6010 from Nusil Technologies, Inc. in a layer with an uncompressed thickness of 0.062 inches.

Figure 4:
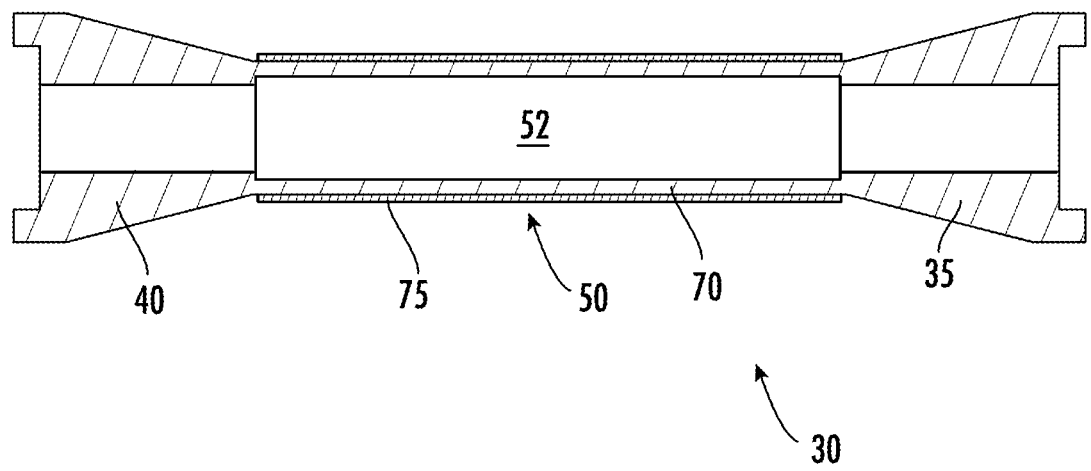
FIG. 4 is a cross section of a connector according to a second embodiment of the present disclosure.

In the embodiment of FIG. 4, the rigid conduit 50, particularly the flexible tube 70 may be co-molded with at least one or both of the first fitting 30 and the second fitting 40.

Figure 5:
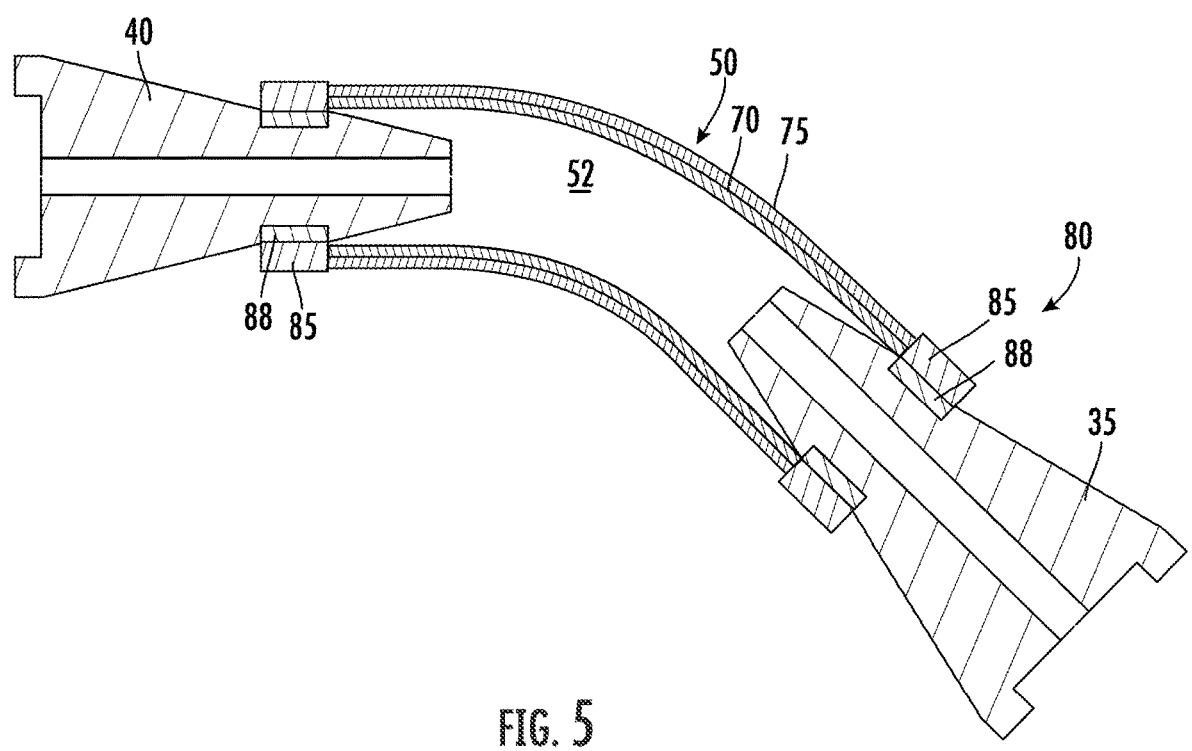
FIG. 5 is a cross section of a connector according to a third embodiment of the present disclosure.

In the embodiment of FIG. 5, the rigid conduit 50 is non-linear between the first and second fittings 35, 40. The rigid conduit 50 may be angled or curved. As shown, the rigid conduit 50 defines a 45-degree bend; however, the non-linear rigid conduit 50 may define a bend in a range of 1 degree to 179 degrees or in a range of 15 degrees to 180 degrees. In particular embodiments, the rigid conduit 50 is a 90-degree elbow. In certain embodiment, the rigid conduit 50 defines a bend in a range of 15 degrees to 90 degrees. The angle of the bend of the rigid conduit 50 is defined by the deformable sleeve 75 that forces the flexible tube 70 to adopt the same angle. By having an angle, the rigid conduit, and thus the entire fluid transfer system may be placed in a location where a linear fluid transfer system would not fit or be appropriate if the rigid conduit 50 was linear.

Returning to FIG. 1, in use, an operator may draw a sample from the first vessel 15, thereby filling the second vessel 20 with a sample. At that point, the operator may desire to disconnect the second vessel 20 from the first vessel 15, without exposing the contents of either vessel to contaminants, such as particles in ambient air. To separate the vessels 15, 20, the operator may apply pressure to the deformable sleeve 75 of the rigid conduit 50, which may be adhesively fixed to flexible tube 70, and deform the deformable sleeve 75 thereby sealing the flexible tube 70. The operator may then apply additional pressure to cut the deformable sleeve 75 and the flexible tube 70 thereby severing the deformable sleeve 75 and the flexible tube 70 and leaving the flexible tube 70 substantially sealed where cut. In one embodiment, the operator quickly applies pressure that substantially seals and then immediately cuts the deformable sleeve 75. The pressure may be applied with a tool such as a pair of snips or wire cutters or any other tool sufficient to crimp and cut the deformable sleeve 75 and flexible tube 70.

Figure 6:
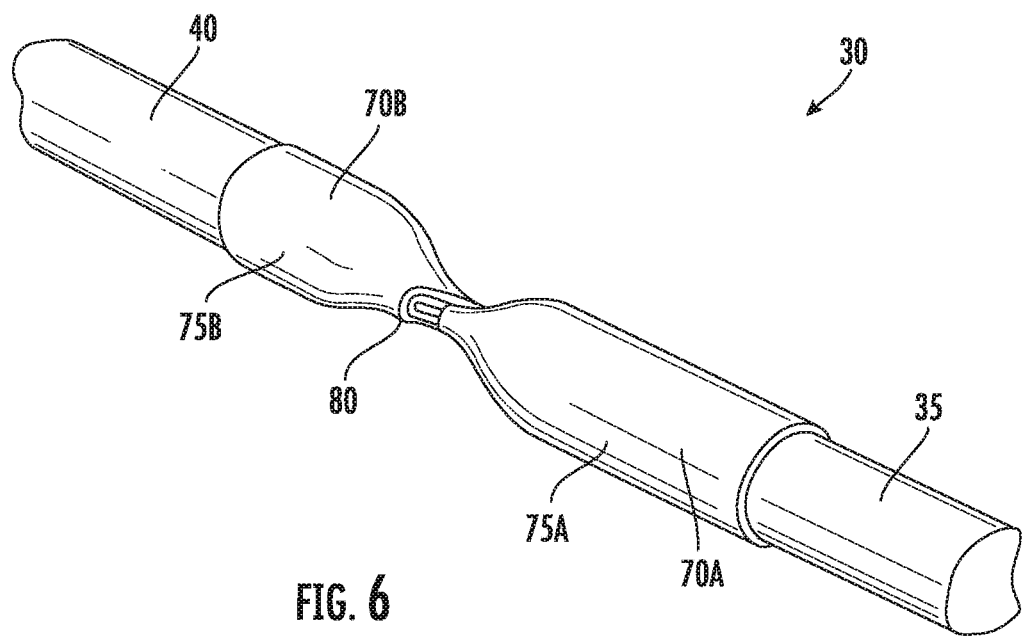
FIG. 6 shows the connector of FIG. 2 in a severed state.

FIG. 6 provides an embodiment of the connector 30 that has been cut or severed. In this cut state, there is provided two pieces of the deformable sleeve 75A and 75B. Likewise, there is now provided two pieces of flexible tube 70A and 70B. One piece of tube may remain attached to the first fitting 35 while the other piece of tube remains attached to the second fitting 40. Once cut, the crimped flexible tube 70 and the deformable sleeve 75 form a seal 90. Due to the physical properties of the flexible tube 70 and the deformable sleeve 75 described in detail above, the flexible tube and the deformable sleeve 75 remain substantially sealed, thereby preventing fluid or other media from leaking.

All dimensional information presented herein and included in the drawings is intended to be illustrative and not intended to limit the scope of the invention. The foregoing descriptions of detachable transfer conduit illustrate and describe various embodiments considered to represent best modes of carrying out the invention. As various changes can be made in the above embodiments without departing from the scope of the detachable transfer conduit disclosed and claimed herein, it is intended that all matter contained in the above description or shown in the accompanying drawings shall be interpreted as illustrative and not limiting. Furthermore, the scope of the invention covers various modifications, combinations, alterations, etc., of the above-described embodiments that all are within the scope of the claims. Additionally, the disclosure shows and describes only selected embodiments of the invention, but the invention is capable of use in various other combinations, modifications, and environments and is capable of changes or modifications within the scope of the inventive concept as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the invention without departing from the scope of the invention.

The invention claimed is:

1. A connector for facilitating fluid transfer, the connector comprising:
   a first fitting suitable for receiving a fluid;
   a second fitting suitable for emitting the fluid;
   a rigid conduit including a flexible tube surrounded by a deformable sleeve and defining a lumen extending therethrough, the deformable sleeve fixed to an outer surface of the flexible tube prior to deformation, the rigid conduit connected on a first end to the first fitting and on a second end to the second fitting, the lumen capable of being sealed;
   a first retaining connector connecting the first fitting to the rigid conduit; and
   a second retaining connector connecting the second fitting to the rigid conduit,
   the flexible tube and deformable sleeve of the rigid conduit capable of being deformed and severed while maintaining the seal of the lumen to separate the first fitting from the second fitting, and the connections of the first and second fittings to the rigid conduit being capable of withstanding at least 1 bar of pressure without leaking.

2. The connector of claim 1, wherein the deformable sleeve is formed of a material having plasticity such that pressure applied to the deformable sleeve causes the deformable sleeve to deform about and seal the flexible tube and upon continued application of pressure to the deformable sleeve, the deformable sleeve and the flexible tube are cut and the deformable sleeve retains a deformed shape substantially sealing the tube.

3. The connector of claim 2, wherein the deformable sleeve is adhesively attached to the flexible tube, wherein the deformable sleeve and adhesive are formed of materials having plasticity such that pressure applied to the deformable sleeve causes the deformable sleeve and adhesive to deform about and seal the flexible tube and upon continued application of pressure to the deformable sleeve, the deformable sleeve, the adhesive, and the flexible tube are cut and the deformable sleeve retains a deformed shape substantially sealing the flexible tube.

4. The connector of claim 3, wherein the flexible tube is integral with at least one of the first fitting or the second fitting.

5. The connector of claim 4, wherein the flexible tube is integral with both the first fitting and the second fitting.

6. The connector of claim 3, wherein the first retaining connector or the second retaining connector includes a clamp that clamps the rigid conduit to a respective one of the first fitting or the second fitting.

7. The connector of claim 3, wherein the first retaining connector or the second retaining connector includes a fastener that connects the rigid conduit to a respective one of the first fitting or the second fitting, the fastener comprising a crimp collar that surrounds an elastomeric liner.

8. The connector of claim 3, wherein the deformable sleeve is attached to the flexible tube with an adhesive selected from the group consisting of a curable platinum catalyzed silicone adhesive, a moisture curable silicone adhesive, a hot melt adhesive, cyanoacrylate, epoxy, and urethane.

9. The connector of claim 8, wherein the rigid tube further comprises a primer between the flexible tube and the adhesive.

10. The connector of claim 1, wherein the deformable sleeve is made of a metal selected from the group consisting of aluminum, anodized aluminum, brass, bronze, nickel-plated bronze, and stainless steel.

11. The connector of claim 1, wherein the deformable sleeve has as wall thickness between 0.005 to 0,062 inches.

12. The connector of claim 1, wherein the flexible tube comprises a thermoplastic elastomer tubing.

13. The connector of claim 12, wherein the flexible tube is constructed from material selected from the group consisting of styrene isobutylene copolymer and ethylene propylene copolymers blended with polypropylene.

14. The connector of claim 1, wherein the flexible tube comprises thermoplastic polymer tubing.

15. The connector of claim 14, wherein the flexible tube is constructed from material selected from the group consisting of polyvinyl chloride (PVC) and a flexible polyolefin.

16. The connector of claim 1, wherein the flexible tube comprises thermoset elastomer tubing.

17. The connector of claim 16, wherein the flexible tube is constructed from material selected from the group consisting of silicone, phenyl silicone, fluoroelastomer (FKM), perfluoroelastomer (FFKM), and perfluoropolyether.

18. The connector of claim 1, wherein the rigid conduit is non-linear between the first and second ends thereof.

19. The connector of claim 1, wherein the rigid conduit includes a bend between the first and second ends thereof.

20. The connector of claim 19, wherein the bend is in a range of 15 degrees to 90 degrees.

21. An aseptic fluid transfer system comprising:
a first vessel;
a second vessel; and
a connector comprising:
   a first fitting in fluid communication with the first vessel;
   a second fitting in fluid communication with the second vessel; and
   a rigid conduit connected between the first fitting and the second fitting, the rigid conduit comprising a flexible tube and a deformable sleeve fixed to the flexible tube prior to deformation, the flexible tube defining a lumen that extends through the rigid conduit and that is capable of being sealed, the flexible tube and the deformable sleeve of the rigid conduit being capable of being severed while maintaining a seal of the lumen to separate the first fitting from the second fitting.

22. A method of aseptically separating a closed fluid transfer system, the closed fluid transfer system including a first vessel, a second vessel, and a fluid transfer connector disposed between the first vessel and the second vessel, the fluid transfer connector having a first fitting suitable for receiving a fluid from the first vessel, a second fitting suitable for emitting the fluid to the second vessel, and a rigid conduit connected between the first fitting and the second fitting, the method comprising:
   applying pressure to the rigid conduit to deform the rigid conduit, the rigid conduit including a deformable sleeve fixed to an outer surface of a flexible tube prior to deformation thereof; and
   applying further pressure to the rigid conduit to cut the deformable sleeve and the flexible tube of the rigid conduit thereby leaving a lumen defined through the rigid conduit substantially sealed where cut.

23. The method of claim 22, wherein the rigid conduit comprises a flexible tube surrounded by a deformable sleeve, the deformable sleeve being adhered to the flexible tube, wherein deforming the rigid conduit comprises deforming the flexible tube and the deformable sleeve, and wherein sealing t rigid conduit comprises sealing the flexible tube.

24. The method of claim 22, wherein the pressure to deform and the pressure to cut is applied simultaneously.

25. A connector for facilitating fluid transfer, the connector comprising:
   a rigid conduit including a flexible tube surrounded by a deformable sleeve, the rigid conduit having a first end, a second end, and a lumen defined therethrough with the flexible tube and the deformable sleeve each extending from the first end to the second end, the rigid conduit configured to seal the lumen when severed;
   a first fitting;
   a second fitting;
   a first retaining connector forming a first connection between the first fitting and the first end of the rigid conduit, the first connection capable of withstanding at least 1 bar of pressure without leaking; and
   a second retaining connector forming a second connection between the second fitting and the second end of the rigid conduit, the second connection capable of withstanding at least 1 bar of pressure without leaking.

26. The connector of claim 25, wherein the rigid conduit is non-linear between the first and second ends thereof.

27. The connector of claim 25, wherein the rigid conduit includes a bend between the first and second ends thereof.

28. The connector of claim 27, wherein the bend is in a range of 15 degrees to 90 degrees.

* * * * *